United States Patent
Hirato et al.

(10) Patent No.: US 9,202,669 B2
(45) Date of Patent: Dec. 1, 2015

(54) CHARGED PARTICLE BEAM DEVICE AND IMAGE DISPLAY METHOD FOR STEREOSCOPIC OBSERVATION AND STEREOSCOPIC DISPLAY

(71) Applicant: HITACHI HIGH-TECHNOLOGIES CORPORATION, Minato-ku, Tokyo (JP)

(72) Inventors: Tatsuya Hirato, Hitachinaka (JP); Hiroyuki Komuro, Hitachinaka (JP); Shigeru Kawamata, Hitachinaka (JP)

(73) Assignee: HITACHI HIGH-TECHNOLOGIES CORPORATION, Tokyo (JP)

(*) Notice: Subject to any disclaimer, the term of this patent is extended or adjusted under 35 U.S.C. 154(b) by 0 days.

(21) Appl. No.: 14/018,919

(22) Filed: Sep. 5, 2013

(65) Prior Publication Data

US 2014/0001355 A1  Jan. 2, 2014

Related U.S. Application Data

(63) Continuation of application No. 13/389,285, filed as application No. PCT/JP2010/062173 on Jul. 20, 2010, now abandoned.

(30) Foreign Application Priority Data

Aug. 10, 2009 (JP) ................................. 2009-185396

(51) Int. Cl.
*G01N 23/00* (2006.01)
*H01J 37/28* (2006.01)
(Continued)

(52) U.S. Cl.
CPC ............. *H01J 37/28* (2013.01); *H01J 37/1478* (2013.01); *A61B 6/022* (2013.01); *G02B 27/2207* (2013.01); *G02B 27/2214* (2013.01); *H01J 37/153* (2013.01); *H01J 2237/2611* (2013.01)

(58) Field of Classification Search
CPC  H01J 31/22; H01J 37/1478; H01J 2237/2611
USPC ............ 250/306, 307, 311, 492.1, 492.3, 397
See application file for complete search history.

(56) References Cited

U.S. PATENT DOCUMENTS 3,852,597 A * 12/1974 Yanaka et al. ................. 250/311
4,437,009 A    3/1984 Yamazaki
(Continued)

FOREIGN PATENT DOCUMENTS

JP    55-48610 U    3/1980
JP    62-198043 A   9/1987
(Continued)

*Primary Examiner* — Nicole Ippolito
*Assistant Examiner* — Jason McCormack
(74) *Attorney, Agent, or Firm* — Mattingly & Malur, PC (57) ABSTRACT

According to the present invention, in a charged particle beam device having a charged particle source, an objective lens for focusing a primary-charged particle beam emitted from the charged particle source, a scan deflector for scanning the primary-charged particle beam on a sample, and a detector for detecting signal particles generated from the sample under scanning of the primary-charged particle beam, whereby a sample image is obtained by using the signal particles of the detector, the charged particle beam device comprises a deflector for deflecting an angle of irradiation of the primary-charged particle beam onto the sample, first and second independent power supplies for passing currents to the deflector, and a switch for switching over voltages applied from the two power supplies in unit of one line or one frame of scanning of the primary-charged particle beam.

5 Claims, 9 Drawing Sheets

(51) Int. Cl.
   *H01J 37/147*  (2006.01)
   *A61B 6/02*    (2006.01)
   *G02B 27/22*   (2006.01)
   *H01J 37/153*  (2006.01)

(56) References Cited

U.S. PATENT DOCUMENTS

| | | | |
|---|---|---|---|
| 4,871,912 A | 10/1989 | Kokubo et al. | |
| 4,983,832 A | 1/1991 | Sato | |
| 7,531,799 B2 | 5/2009 | Kawasaki et al. | |
| 7,973,282 B2* | 7/2011 | Sato et al. | 250/311 |
| 8,129,693 B2 | 3/2012 | Preikszas | |
| 8,153,969 B2 | 4/2012 | Fukada et al. | |
| 2001/0050338 A1 | 12/2001 | Nomura | |
| 2002/0179812 A1* | 12/2002 | Kochi et al. | 250/200 |
| 2003/0201393 A1 | 10/2003 | Tsuneta et al. | |
| 2005/0061973 A1* | 3/2005 | Kazui et al. | 250/310 |
| 2005/0078108 A1* | 4/2005 | Swift et al. | 345/419 |
| 2006/0033037 A1* | 2/2006 | Kawasaki et al. | 250/398 |
| 2007/0158568 A1* | 7/2007 | Nakamura et al. | 250/311 |
| 2008/0099673 A1* | 5/2008 | Fukuda et al. | 250/307 |
| 2008/0237456 A1 | 10/2008 | Miyamoto et al. | |
| 2009/0322973 A1* | 12/2009 | Ito et al. | 349/15 |
| 2010/0033560 A1 | 2/2010 | Kawasaki et al. | |
| 2010/0264309 A1* | 10/2010 | Hirose et al. | 250/310 |

FOREIGN PATENT DOCUMENTS

| | | | |
|---|---|---|---|
| JP | 02-033843 A | | 2/1990 |
| JP | 5-2364 U | | 1/1993 |
| JP | 2000-102037 A | | 4/2000 |
| JP | 2000-284223 A | | 10/2000 |
| JP | 2007-026885 A | | 2/2007 |
| JP | 2007-49598 A | | 2/2007 |
| JP | 2007-234620 A | | 9/2007 |
| JP | 2008159286 A | * | 7/2008 |
| JP | 2008-298480 A | | 12/2008 |

* cited by examiner

CHARGED PARTICLE BEAM DEVICE AND IMAGE DISPLAY METHOD FOR STEREOSCOPIC OBSERVATION AND STEREOSCOPIC DISPLAY

This application is a continuation of U.S. patent application Ser. No. 13/389,285, filed Feb. 7, 2012, which is a 371 of International Application No. PCT/JP2010/062173, filed Jul. 20, 2010, which claims priority to Japanese Patent Application No. 2009-185396, filed Aug. 10, 2009, which is incorporated herein by reference in its entirety.

TECHNICAL FIELD

The present invention relates to a charged particle beam device and an image display method thereby and more particularly, to a method for structuring a three-dimensional image in a charged particle beam device provided with a stereo pair image observing function.

BACKGROUND ART

When capturing a three-dimensional image, the charged particle beam device typified by a scanning electron microscope displayed two images alternately by using two sheets of images for left eye and for right eye which are captured in directions at different angles (cited literature 1) or conducted a stereoscopic observation through a cross method, a parallel method or an anaglyph method using a pair of red and blue spectacles.

Also, in recent years, a scheme of obtaining a tilt image of a sample by tilting a charged particle beam in relation to the sample (patent literature 2) and a stereoscopic liquid crystal display for use in a three-dimensional image display method as well have been developed and therefore, techniques applicable to stereoscopic observation have been developed in the respective technical fields.

CITATION LIST

Patent Literature

Patent Literature 1: JP-U-55-48610
Patent Literature 2: JP-A-2-33843

SUMMARY OF INVENTION

Technical Problem

In the aforementioned conventional techniques laid open to public, a stereoscopic image is structured from parallax images making right/left uniform angles to the optical axis center (for example, ±3°) in only one axis direction (for example, X direction) and consequently, a stereoscopic image as viewing a sample from directly above can only be obtained.

Conceivably, a stereoscopic image as viewing from another direction (for example, from obliquely above) can be obtained by tilting or rotating a sample stage but a problem of time to set a sample stage mechanically or a drift of observation position will become apprehensive, making the operation complicated.

In addition, different stereoscopic observation methods have features as below, respectively, and which one of the observation methods is superior cannot generally be determined.

The cross method and parallel method do not require dedicated tools and permit stereoscopic view to be effected with naked eyes but these methods are unsuited for ordinary operation, raising necessity for training and not a small numbers of operators are ill fitted for these methods.

Further, the anaglyph method permits stereoscopic observation without making a request for training but constantly requires a pair of red and blue spectacles, having problems of unsuitability to ordinary operation and of a degradation in brightness attributable to a color filter.

Furthermore, the stereoscopic liquid crystal display does not require training and can permit stereoscopic observation to be effected with naked eyes, thus hardly hindering the ordinary operation but it needs an installation space and is expensive.

As described above, the individual observation methods have advantages/disadvantages and different operators are skilful at or ill fitted to them, demonstrating that if a stereoscopic observation method can be selected freely, facilitation of the usage can be improved.

An object of the present invention is to provide capture means for acquiring right and left parallax images from not only directly above but also obliquely above. Besides, parallax image display means and an operation screen which are able to switch over stereoscopic observation methods are provided.

Solution to Problem

According to the present invention, a charged particle beam device having a charged particle source, an objective lens for focusing a primary-charged particle beam emitted from the charged particle source, a scan deflector for scanning the primary-charged particle beam on a sample, and a detector for detecting signal particles generated from the sample under scanning of the primary-charged particle beam, whereby a sample image is obtained by using the signal particles detected by the detector, comprises a deflector for deflecting an angle of irradiation of the primary-charged particle beam on the sample, first and second independent power supplies for passing currents to the deflector, and a switch for switching over the two power supplies in unit of one line or one frame of scanning of the primary-charged particle beam.

Also, according to the present invention, a charged particle beam device having a charged particle source, an objective lens for focusing a primary-charged particle beam emitted from the charged particle source, a scan deflector for scanning the primary-charged particle beam on a sample and a detector for detecting signal particles generated from the sample under scanning of the primary-charged particle beam, whereby a sample image is obtained by using the signal particles detected by the detector, comprises a deflector for deflecting an angle of irradiation of the primary-charged particle beam on the sample, the deflector being applied with two different voltages to obtain a first image and a second image, and a display unit for displaying the first image and the second image, wherein locations on the display unit at which the first image and the second image are displayed on the display unit are switched over.

Advantageous Effects of Invention

With the above construction, a charged particle beam device can be provided which can obtain a stereoscopic image viewing from not only directly above but also obliquely above. Besides, parallax image display means and an observation screen which are able to switch over stereoscopic observation methods can be provided and the user can select the observation direction, parallax angle and stereoscopic observation method through mouse operation alone.

Other objects, features and advantages of the present invention will become apparent from the following description of embodiments of the invention taken in conjunction with the accompanying drawings.

DESCRIPTION OF EMBODIMENTS

Embodiments of the present invention will be described hereunder by making reference to drawings.

Figure 1:
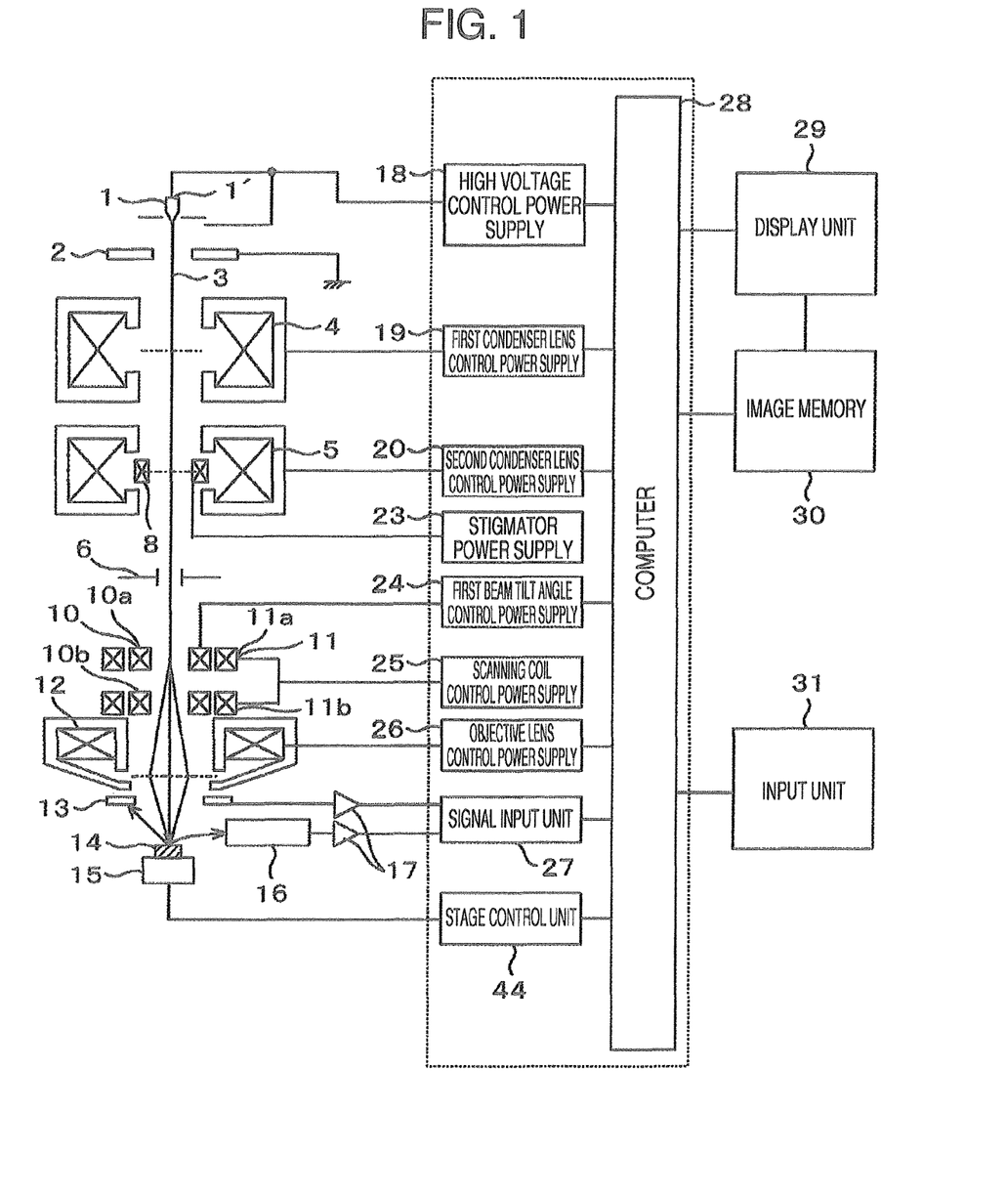
FIG. 1 is a diagram schematically illustrating a scanning electron microscope representing an example of the present invention.

FIG. 1 is a diagram schematically illustrating a scanning electron microscope representing an example of the present invention.

Across a cathode 1 and an anode 2 constituting an electron gun 1' representing a charged particle beam source, a voltage is applied from a high voltage control power supply 18 which is controlled by a computer 28 representing a control unit, a primary-electron beam 3 representing a primary-charged particle beam is extracted from the cathode 1 and is then accelerated through an anode for acceleration (not shown) so as to be led to a lens system of the succeeding stage.

The primary-electron beam 3 is converged by means of a first condenser lens 4 controlled by a first condenser lens control power supply 19, further converged by means of a second condenser lens 5 controlled by a second condenser lens control power supply 20, removed of an unnecessary region of primary-electron beam 3 by means of an aperture plate 6 and thereafter, led to a beam tilt angle control coil 10 controlled by a primary-beam tilt angle control power supply 24. The beam tilt angle control coil 10 is constituted by an upper deflection coil 10a and a lower deflection coil 10b. Disposed above the beam tilt angle control coil 10 is a stigmator coil 8 having the function to be described later. To add, the stigmator coil 8 is subjected to current control with the help of a stigmator power supply 23.

The aforementioned beam tilt angle control coil 10 is disposed above an objective lens 12 controlled by means of an objective lens control power supply 26 and besides, around the beam tilt angle control coil 10, a scanning coil 11 of upper and lower two stages (11a, 11b) is arranged which is adapted to scan the primary-electron beam 3 on a sample 14 mounted on a sample holder (not shown). The scanning coil 11 is controlled by means of a scanning coil control power supply 25. The sample holder mounting the sample 14 can be moved in directions on XY plane or in Z direction by means of a sample stage 15, thereby ensuring that a primary-electron beam scanning area, that is, a field of view on the sample can be moved. Movement of the sample stage 15 is controlled by a stage control unit 44.

Horizontal direction deflection current and vertical direction deflection current for the primary-electron beam 3 can be controlled through the scanning coil 11 by means of the scanning coil control power supply 25 and the primary-electron beam 3 can undergo two-dimensional scan control on the sample 14. Secondary electrons generated from the sample 14 under irradiation of the primary-electron beam 3 are separated from the primary-electrons by means of an orthogonal electromagnetic field generator for secondary electron separation (not shown) and detected with the help of a secondary electron detector 16. Signals detected by the secondary electron detector 16 are amplified with a signal amplifier 17 and then inputted to the computer 28 by way of a signal input unit 27.

Backscattering electrons of primary-electron beam 3 from the sample surface are also detected with a backscattered electron detector 13, amplified with another signal amplifier 17 and subsequently, inputted to the computer 28 by way of the signal input unit 27. The backscattered electrons are also image-processed to a backscattered electron image by means of the computer 28 and can be displayed through a display unit 29.

It is to be noted that a reference sign 31 designates an input unit in which image take-in conditions (such as switchover operation between two-dimensional observation mode and three-dimensional observation mode, scanning speed, accelerating voltage and so on) are set.

In the present embodiment, the computer (control unit) 28 controls currents of beam tilt angle control coil 10 and scanning coil 11 by way of the primary-beam tilt angle control power supply 24 and scanning coil control power supply 25, so that in executing three-dimensional observation on real time base, the direction of sample observation can be changed without resort to additionally conducting mechanical operation of the sample stage 15 in association with the beam tilt angle control coil 10.

A three-dimensional observation on real time base will be described below.

By controlling the primary-charged particle beam (for example, such a charged particle beam as an electron beam or ion beam) 3 such that two scanning operations of left tilting scan and right tilting scan corresponding to a parallax angle are carried out on the same line of scanning on the sample by switching over left and right parallax images in unit of one line or in unit of one frame, these images are obtained on real time base and stored in an image memory 30. In other words, the computer 28 synthesizes a left tilting beam scanning image on the basis of secondary electron detection signals obtained through scans in odd orders, namely, through left tilting primary-electron beam scans and also synthesizes a right tilting beam scanning image on the basis of secondary electron detection signals obtained through scans in even orders, namely, through right tilting primary-electron beam scans. Then, these left and right parallax images are three-dimensionally processed and three-dimensional observation on real time base is executed.

Figure 2:
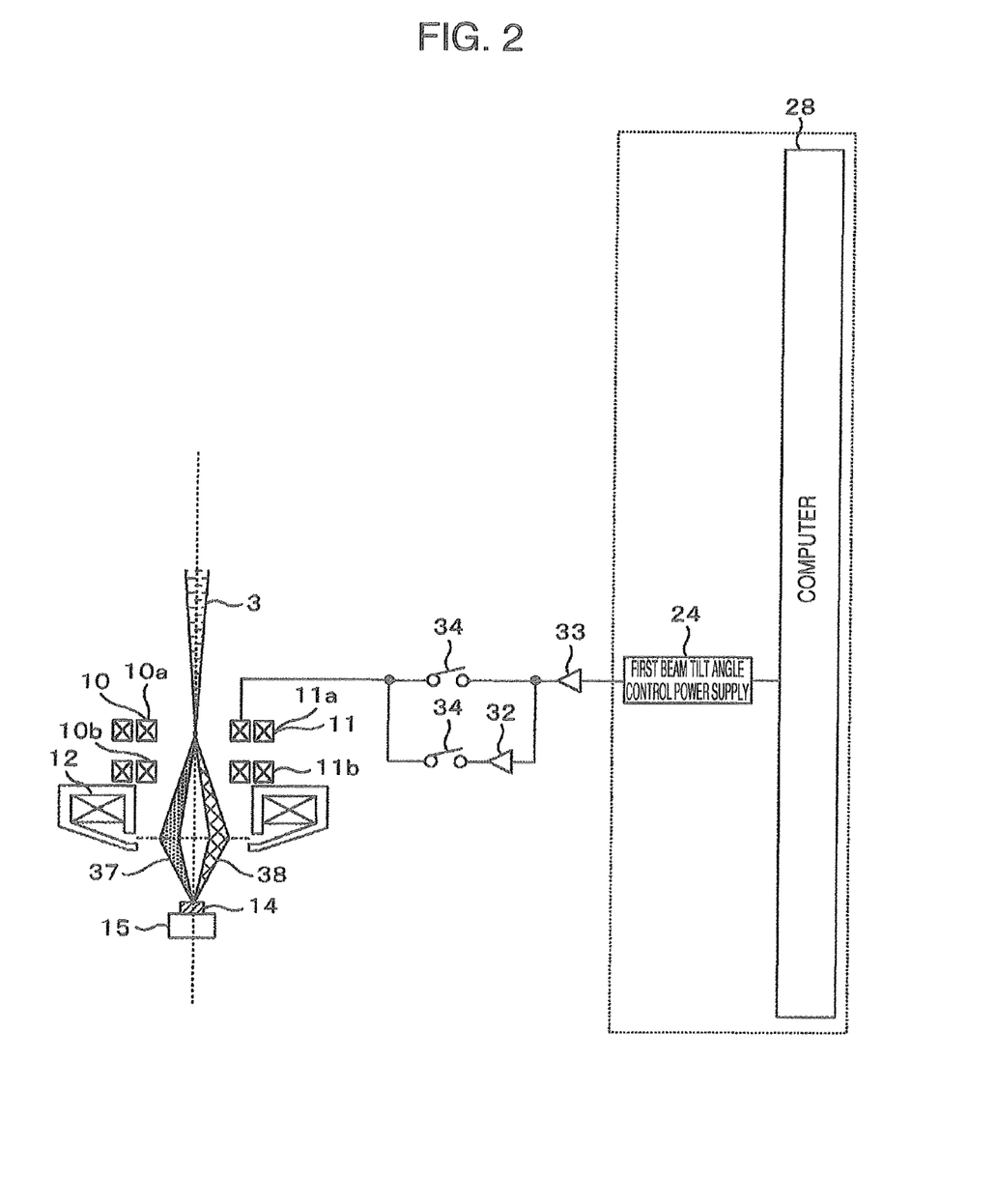
FIG. 2 shows means which tilts symmetrically without tilting the beam center.

Referring to FIG. 2, means which tilts the beam symmetrically to the center axis is illustrated. A reference sign 37 designates a tilting beam trajectory for left eye (left tilting) and a reference sign 38 designates a tilting beam trajectory for right eye (right tilting).

In order to obtain left and right parallax images, a signal from the primary-beam tilt angle control power supply 24 is amplified with a tilting signal amplifier 33 and an amplified signal is switched over by means of a tilt direction transfer switch 34 in unit of one line or in unit of one frame. In this case, an inversion input element 32, for example, is provided for a right tilting side so that a left tilt signal may be inverted and inputted to a right tilt side so as to pass a plus-minus current to the beam tilt angle control coil 10, with the result that the beam can be tilted symmetrically to the center axis. In other words, when tilting the beam right and left, a current of 1 A, for example, is passed to the beam tilt angle control coil 10 at the time of left tilting and then, at the time of right tilting, the current value is inverted and a current of −1 A is passed. With this construction, the beam is centered on the center axis and a stereoscopic image as viewing the sample from directly above can be formed.

A further description will be given of a method for forming a three-dimensional image when the sample is viewed from obliquely above.

Figure 3:
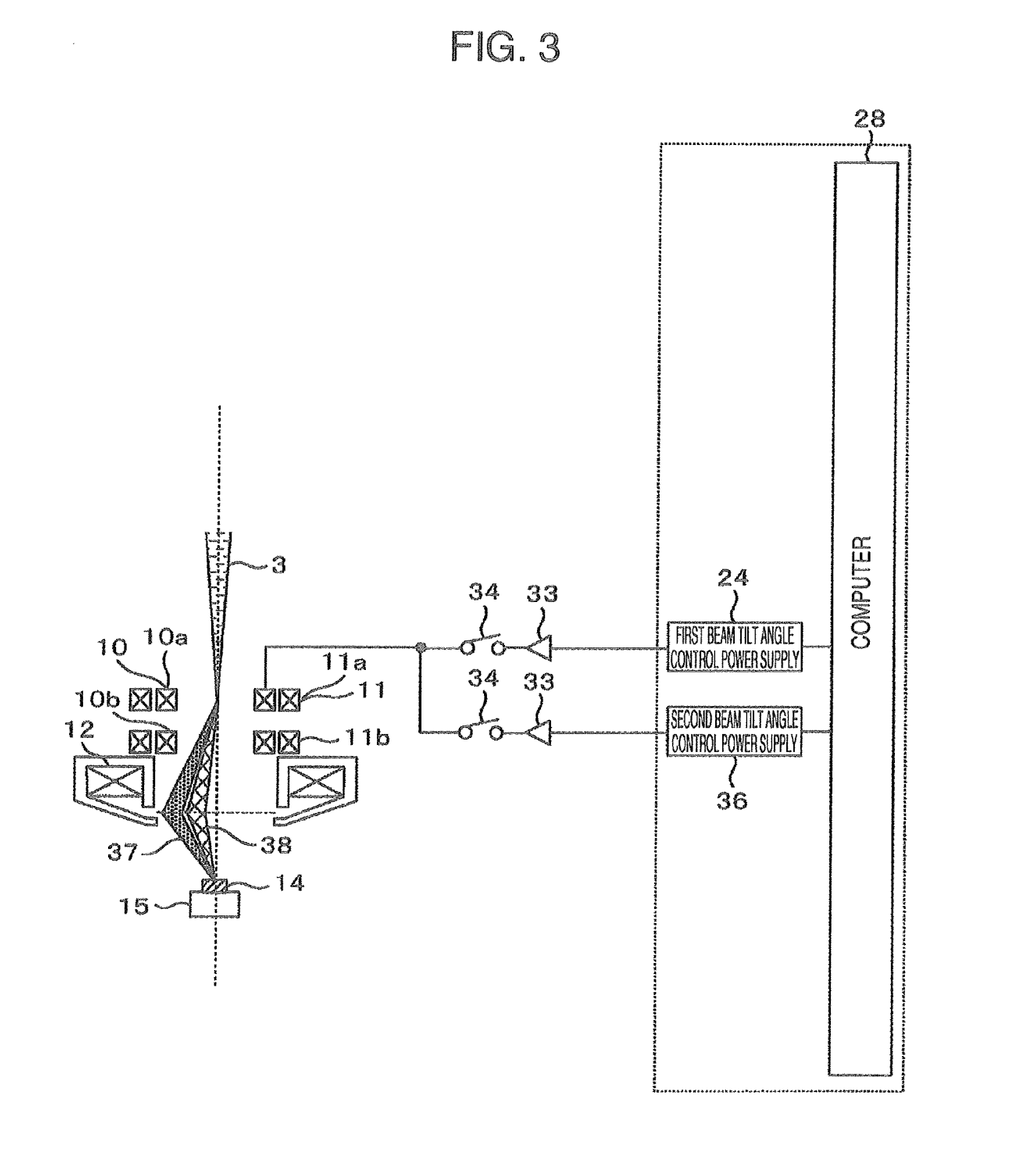
FIG. 3 shows means which captures parallax images independently by tilting the beam center.

As shown in FIG. 3, a second beam tilt angle control power supply 36 is newly arranged to provide control based on independent two systems by using tilt signal amplifiers 33 so as to permit left and right tilts to have independent control values. With this construction, the plus-minus current is not passed to the beam tilt angle control coil 10 but both of plus currents or both of minus currents are passed, thus making it possible to form a stereoscopic image when the sample is viewed from obliquely above. It will be appreciated that while both the first beam tilt angle control power supply 24 and the second beam tilt angle power supply 36 are provided, this is not limitative and the formation method can also be materialized with a single control power supply by performing switchover between values by means of a DAC.

Figure 4A:
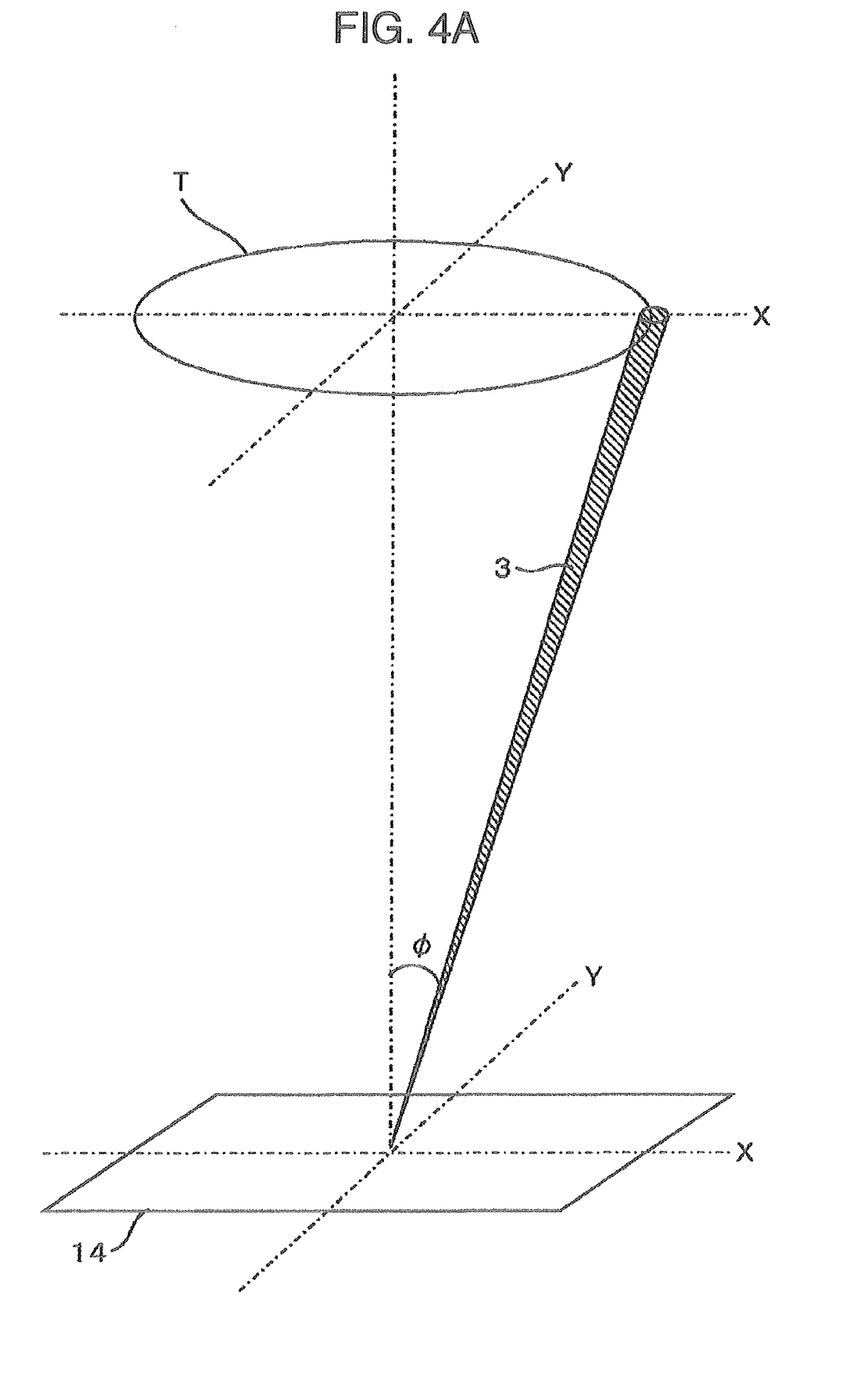
FIG. 4A is a diagram for explaining beam tilting (x direction).
Figure 4B:
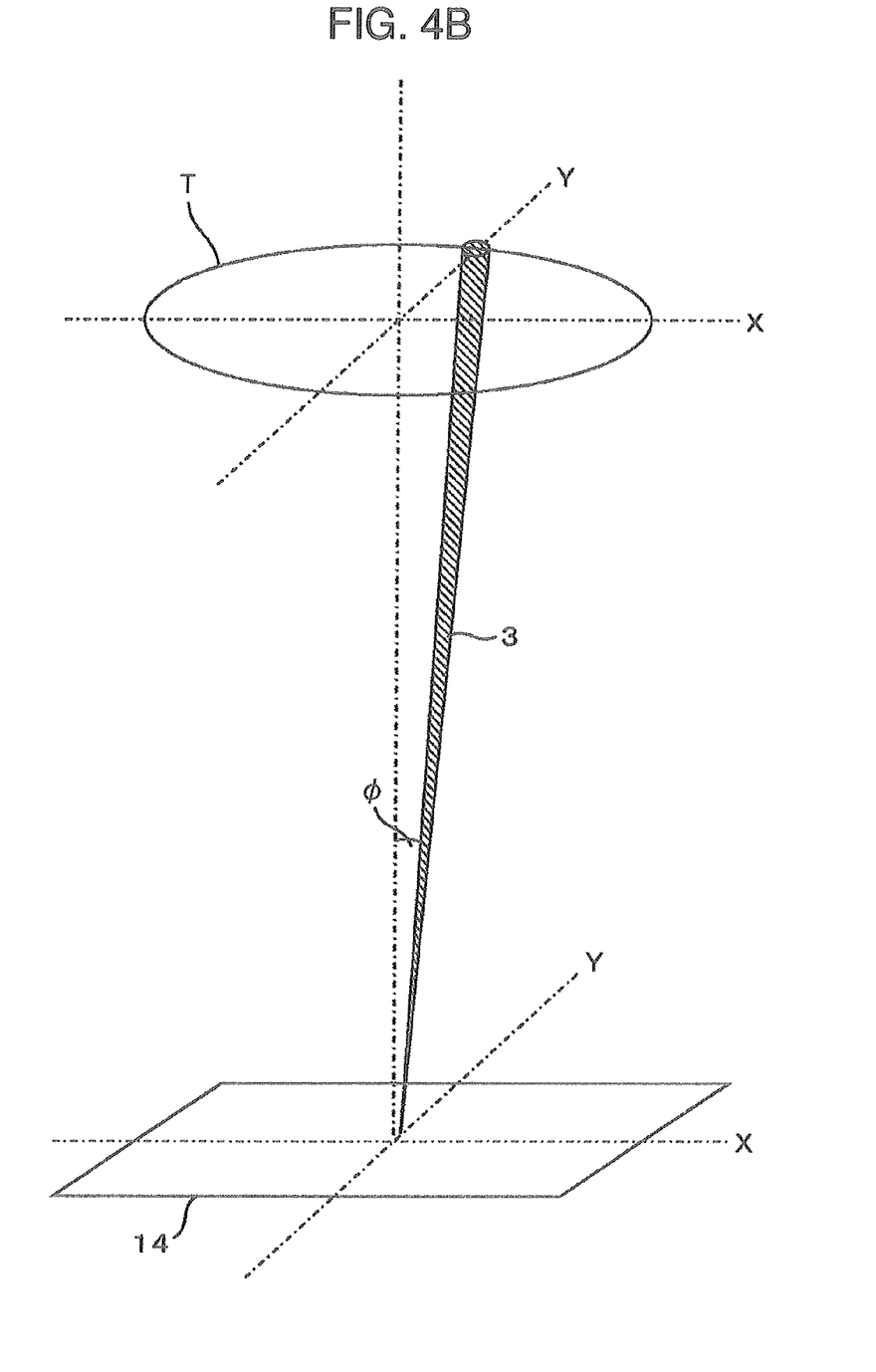
FIG. 4B is a diagram for explaining beam tilting (y direction).
Figure 4C:
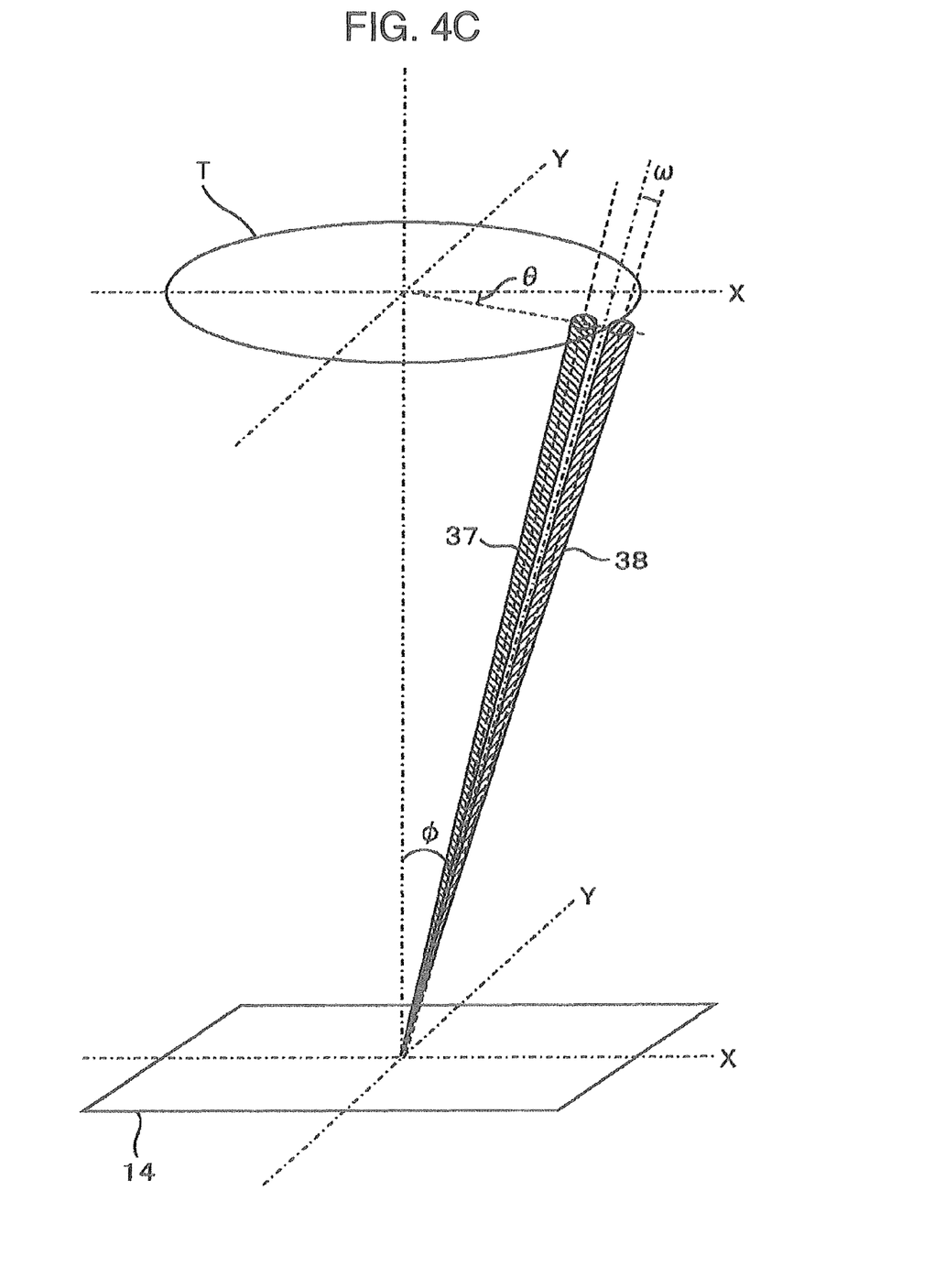
FIG. 4C is a diagram for explaining beam tilting (tilt angle ϕ, rotation angle θ, parallax angle ω).

Turning to FIG. 4A to 4C, the beam tilting pursuant to the aforementioned scheme is diagrammatically outlined. Designated by θ, φ and ω are rotation angle, tilt angle and parallax angle, respectively. Further, T designates an orbit of observation direction when the observation angle is φ. The primary beam trajectory center axis corresponds to the conventional center axis. With a value of φ designated, a concentric circle centered on the conventional center axis is drawn virtually and by designating a value of θ, a beam tilt direction is determined. Furthermore, by designating a parallax angle, a tilt beam trajectory 37 for left eye and a tilt beam trajectory 38 for right eye are introduced and by passing currents corresponding to the parallax angles to the beam tilt angle control coil 10, the sample 14 can be observed stereoscopically in a direction of observation the user desires.

FIG. 4A is a diagram illustrating that the primary beam is tilted through a tilt angle of φ in x direction. In this phase, it is assumed that the amount of current to be passed through an x coil of bream tilt angle control coil 10 is Ix. FIG. 4B is a diagram illustrating that the primary beam is tilted through a tilt angle of φ in y direction. In this phase, it is assumed that the amount of current to be passed through a y coil of bream tilt angle control coil 10 is Iy.

FIG. 4C illustrates an instance where the tilt angle is φ, the rotation angle is θ and the parallax angle is ω. In this case, the current value to be passed during right tilting to the x coil is determined by Ix·(sin(φ+ω)/sin(φ))·cos θ and that to the y coil is determined by Iy·(sin(φ+ω/sin(φ))·sin θ. The current value to be passed during left tilting to the x coil is determined by Ix·(sin(φ−ω)/sin(φ))·cos θ and that to the y coil is determined by Iy·(sin(φ−ω)/sin(φ))·sin θ.

Figure 5:
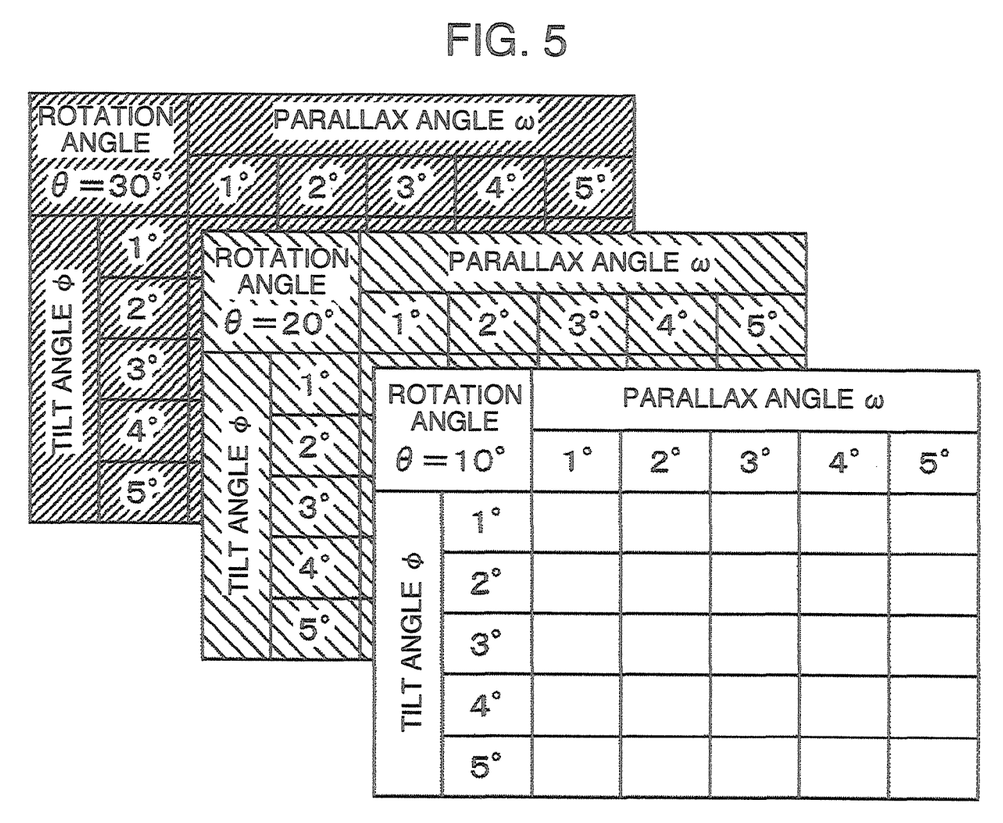
FIG. 5 shows an example of a control table.

Then, by using a control table as shown in FIG. 5 determined from trigonometric functions in x direction and y direction and experiments, the user can engage in easy operation. When the user designates a rotation angle θ, a tilt angle φ and a parallax angle ω, the computer 28 operates to supply current values stored in the control table to the beam tilt angle control coil. If a meeting rotation angle, for example, is not present in the control table, the computer 28 calculates the meeting value through, for example, interpolation.

As a method for changing the observation direction without resort to the aforementioned improvement, a method of tilting/rotating the sample stage 15 is conceivable accompanied by disadvantages of a prolonged time to set a desired position and of a drift of observation position. But, the aforementioned improvement may be considered to be used in combination with the tilting/rotation of the sample stage to attain an advantage (for example, alleviation of resolution degradation attributable to beam tilting) and the combined use can broaden the application range of the device.

(Problem Upon Off-Axis Deflection and Position of Stigmator Coil)

In order to obtain a desired parallax angle on the sample, the beam is caused to be incident on a position distant from the main axis of objective lens to make use of a beam swing back function the lens has, as disclosed in the aforementioned patent literature publicly known. However, when passing through the off-axis region of stigmator coil 8, the beam undergoes the deflection action to affect the beam tilt angle. Further, when a beam being off from the objective lens main axis is incident, the resolution is degraded owing to a spherical aberration essential of the objective lens and also to a blur attributable to an aberration considered as deriving from a chromatic aberration.

An expedient considered to be useful when stereoscopic observation is conducted with the construction as above will be described. An example of arrangement of the stigmator coil 8 in the present invention shown in FIG. 1 will be explained.

The stigmator coil 8 is arranged at a position where its correction function is effective and it does not affect the tilt angle. Mores specifically, since it needs to be arranged at a position where the shape of beam can be formed easily and also the deflection function hardly occurs, it is arranged at a position above the beam tilt angle control coil 10 where the beam is not yet off axis. With this arrangement, the correction for astigmatism is effective and besides, the deflection function hardly occurs to hardly affect the tilt angle.

In addition, the beam can be scanned without being subject to the parallax angle beam tilting to switch the charged particle beam device to ordinary operation and then, the stigmator coil 8 can be used.

Next, a parallax image display program and an operation screen which are able to permit the stereoscopic observation method to be switched over will be described.

Figure 6:
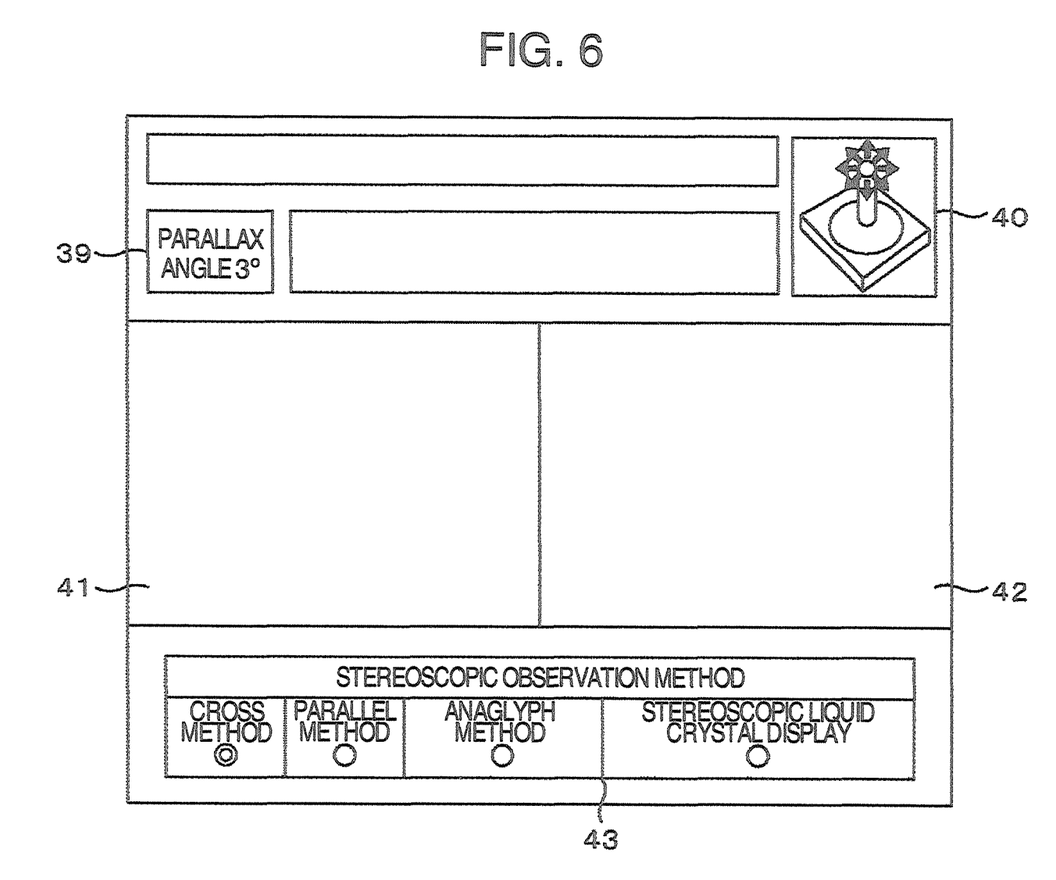
FIG. 6 shows an example of arrangement of an operation screen of a charged particle beam device exemplifying the present invention.

FIG. 6 illustrates an operation screen in the charged particle beam device exemplifying the present invention. A parallax angle designating spot 39 and an observation direction designating spot 40 are located and when individual spots are designated and corresponding values are called out of the control table as shown in FIG. 5 to control current to be passed to the beam tilt angle control coil 10, the user can designate a parallax angle and an observation direction easily.

Designation of observation direction is not limited to be done on the operation screen only but hardware such as, for example, joystick can substitute therefor. Putting the stereoscopic observation aside, the beam can be tilted by using an operation panel as shown in FIG. 6 even during ordinary observation so that a two-dimensional sample tilting image can be captured instantaneously without tilting the sample stage 15, finding an application even during ordinary observation.

For watching a stereoscopic image of a sample, a stereoscopic liquid crystal display is available.

Recently, the stereoscopic liquid crystal display using a dedicated glass has been changing to that of a scheme achieving stereoscopic view with naked eyes. Generally, the use of the dedicated glass can be acceptable when three-dimensional observation is effected constantly in the field of game operation and media appreciation but in the charged particle beam device, an operation other than the three-dimensional observation such as device adjustment and setting of observation conditions and the three-dimensional observation operation as well need to be repeated frequently and therefore, wearing/un-wearing of the dedicated glass is troublesome and spectroscopic view with naked eyes is desired.

The naked-eye stereoscopic liquid crystal display can be classified principally to two types according to its scheme. In one type, a slit-shaped liquid crystal shutter called a parallax barrier is disposed in a liquid crystal panel and coincidentally with the parallax barrier, pieces of image data corresponding to left and right eyes are arranged pixel by pixel and in the other type, a semicircular beam division lens (lenticular) having directivity is disposed in front of the liquid crystal panel and coincidentally with the lens, pieces of image data corresponding to left and right eyes are arranged pixel by pixel. To conduct stereoscopic view with the stereoscopic liquid crystal display, pieces of left and right view pixel data are inputted coincidentally with the pixel arrangement of display. In this scheme, since image data corresponding to left/right parallax can be detected alternately in unit of one line of scanning line, the left/right parallax pixel data pieces are recorded in a line memory of two lines and their arrangement is converted so as to be outputted in compliance with a display rate of the display, so that stereoscopic view on real time base can be conducted.

The example of stereoscopic observation using the stereoscopic liquid crystal display has been described so far but a method for enabling the stereoscopic view to be conducted more easily will be described hereinafter. Images corresponding to left and right parallax are arrayed laterally and on the basis of cross eye or long sight called cross method or parallel method, the left and right images are viewed with the corresponding eyes so as to be overlapped, thus enabling stereoscopic view to be conducted. In this case, pieces of image data corresponding to left and right parallax inputted in unit of one line of scanning line are simply arrayed two-dimensionally right and left. Another method is called anaglyph using a pair of red and blue spectacles, according to which left and right view images are colored with corresponding glass color and overlapped on a general display so as to be displayed.

Incidentally, the individual stereoscopic observation methods have their own features as below and which one of the observation methods is suitable mostly depends on an observer.

The stereoscopic liquid crystal display does not require training, thus hardly hindering the ordinary operation and can permit stereoscopic observation to be effected with naked eyes but it needs an installation space and is expensive.

The cross method and parallel method do not require dedicated tools and permit stereoscopic view to be effected with naked eyes but because of cross eye and distant sight, these methods are unsuited for ordinary operation, raising necessity for training and not a small numbers of operators are ill fitted for either method.

Further, the anaglyph method permits stereoscopic observation without making a request for training but constantly requires a pair of red and blue spectacles for stereoscopic observation, having apprehension of unsuitability to ordinary operation because of wearing/un-wearing of glass and degradation in brightness attributable to a color filter.

Then, in addition to the aforementioned observation direction designation spot 40 and parallax angle designation spot 39, a stereoscopic observation method selection spot 43 for selection of the stereoscopic liquid crystal display/cross method/parallel method and anaglyph method is arranged on the operation screen of FIG. 6. This may be substituted by hardware such as, for example, a switch. Specifically, by arranging, on the operation screen in the charged particle beam device, a first display area 41 capable of displaying a plane image of one of the left and right parallax image data pieces and a second display area 42 capable of displaying the other data piece in order that the left and right parallax images can be displayed on the same screen, permitting an image for right eye and an image for left eye to be displayed, for example, on the first display area 41 and the second display area 42, respectively, and by locating the first display area 41 on the left side and the second display area 42 on the right side, stereoscopic observations can be executed on real time base through the cross method.

The aforementioned stereoscopic observation method selection spot 43 arranged on the operation screen is switched over by means of a button, for instance. In FIG. 6, the cross method is selected as an example.

It is now possible that by depressing a switchover button for parallel method, the control DAC value of tilting current is inverted internally, by physically inverting timing for switching tilt angle switchover, the current passed to the coil adapted to tilt the charged particle beam is inverted or by inverting timing for left and right scanning, an image for left eye is displayed on the first display area 41 and an image for right eye is displayed on the second display area 42, thus completing switchover to the parallel method in an instant.

Also, by depressing a switchover button of anaglyph to color left and right parallax images with corresponding glass colors, respectively, so as to give an overlap display, a stereoscopic observation pursuant to anaglyph can be conducted.

Further, by depressing a switchover button of stereoscopic liquid crystal display to input left/right parallax pixel data in coincidence with pixel arrangement of stereoscopic liquid crystal display (parallax barrier scheme, beam division (lenticular) scheme and so on), a stereoscopic observation by mean of the stereoscopic liquid crystal display can be executed.

In this manner, the user can designate a self-suited stereoscopic observation method with ease.

Figure 7:
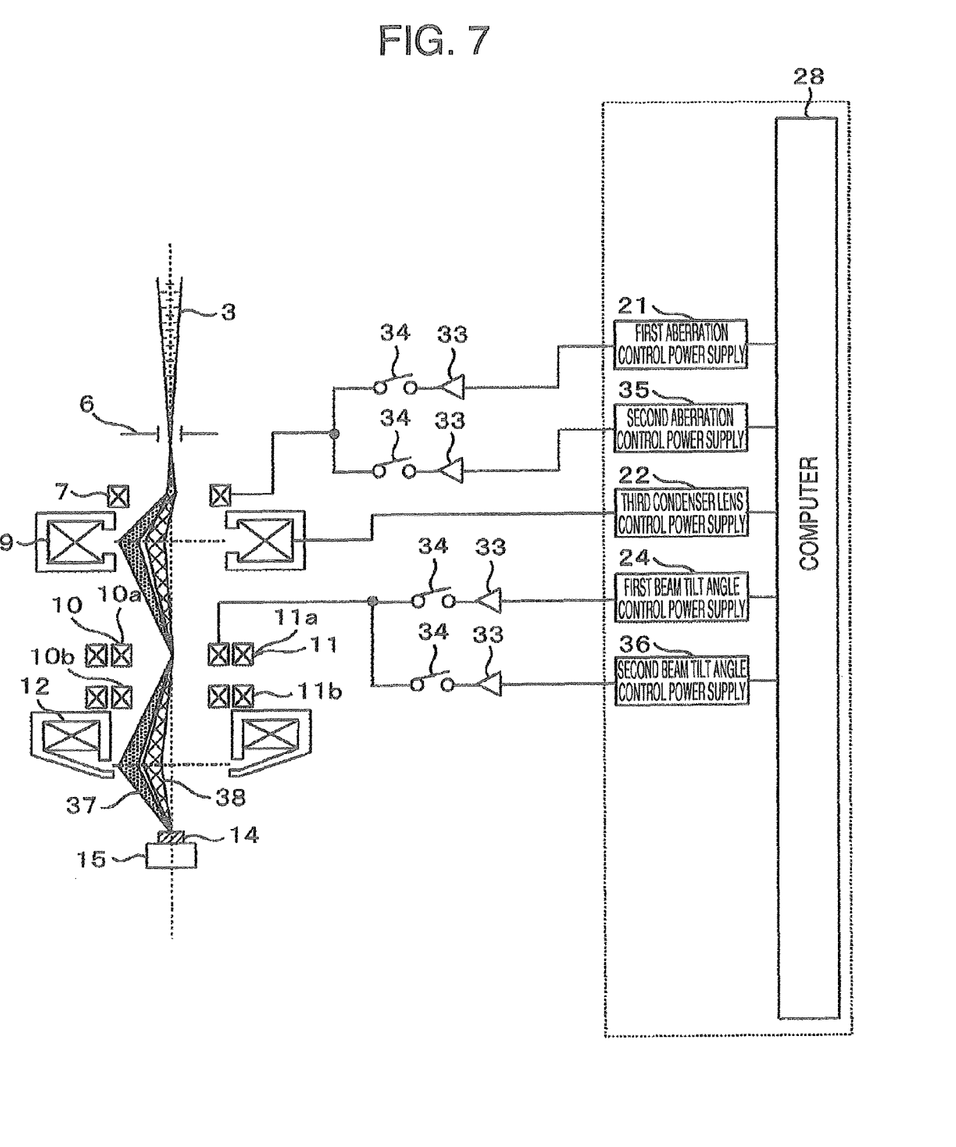
FIG. 7 is a diagram of an example to which the present invention is applied wherein aberrations liable to be generated on a sample by off-axis beams incident on an objective lens are cancelled out totally by an optical system of a plurality of stages of lenses.

In the present invention, as shown in FIG. 7, a third condenser lens (aberration correction lens) 9 controlled by means of a third condenser lens control power supply 22 is further provided below the first condenser lens 4 and second condenser lens 5 (not illustrated in FIG. 7) and besides, a first aberration control power supply 21 and a second aberration control power supply 35 are provided for an electromagnetic coil 7 for forming parallax angles which is arranged above the third condenser lens 9. By performing independent control of two systems as in the case of the previously-described beam tilt angle control coil 10 and by interlocking the control to the beam tilt angle control coil 10, off-axis aberration of the objective lens and aberration of the third condenser lens (aberration correction lens) 9 can be cancelled out with each other under the condition of execution of the present invention, thereby ensuring that an aberration blur attributable to off-axis can be cancelled out.

Further, when the aberration blur is expected to be small as in the case of the tilt angle being shallow, the beam is tilted by using only the beam tilt angle control coil 10 without resort to the parallax angle forming electromagnetic coil 7. The blur can be considered to be removed to some extents by using only the stigmator coil 8 without resort to canceling out of aberration and therefore, either aberration cancel-out or astigmatism correction is used purposely separately or both of them are used in accordance with the situations, improving easiness of usage. At that time, the stigmator coil 8 is arranged above the parallax angle forming electromagnetic coil 7.

While the foregoing description has been given of the embodiments, the present invention is not limited thereto and it will be obvious to those skilled in the art that various changes or alternations and modifications can be made without departing from the sprits of the present invention and within the scope of the appended claims.

REFERENCE SIGNS LIST

1 Cathode
1' Electron gun
2 Anode
3 Primary-electron beam
4 First condenser lens
5 Second condenser lens
6 Aperture plate
7 Parallax angle forming electromagnetic coil
8 Stigmator coil
9 Third condenser lens (aberration correction lens)
10 Beam tilt angle control coil
11 Scanning coil
12 Objective lens
13 Backscattering electron detector
14 Sample
15 Sample stage
16 Secondary electron detector
17 Signal amplifier
18 High voltage control power supply
19 First condenser lens control power supply
20 Second condenser lens control power supply
21 First aberration control power supply
22 Third condenser lens control power supply
23 Stigmator power supply
24 First beam tilt angle control power supply
25 Scanning coil control power supply
26 Objective lens control power supply
27 Signal input unit
28 Computer
29 Display unit
30 Image memory
31 Input unit
32 Inverted input element
33 Tilt signal amplifier
34 Tilt direction switchover switch
35 Second aberration control power supply
36 Second beam tilt angle control power supply
37 Beam trajectory for left eye
38 Beam trajectory for right eye
39 Parallax angle designation spot
40 Observation direction designation spot
41 First display area
42 Second display area
43 Stereoscopic observation method selection spot
44 Stage control unit

The invention claimed is:

1. A charged particle beam device comprising:
a charged particle source;
an objective lens which focuses a primary-charged particle beam emitted from said charged particle source;
a scan deflector which scans said primary-charged particle beam in lines on a sample; and
a detector which detects signal particles generated from the sample under scanning of said primary-charged particle beam, whereby a sample image is obtained by using the signal particles of said detector;
a tilt deflector which deflects said primary-charged particle beam at an angle of irradiation onto the sample;
a switch that switches a state of an angle of irradiation between a first state and a second state on a same line of scanning of said primary-charged particle beam; and
a computer coupled to a display,
wherein the computer displays, on the display, a first button to select a cross method or a parallel method in which a first sample image obtained at the first state of the angle of irradiation and a second sample image obtained at the second state of the angle of irradiation are arrayed laterally and displayed, wherein the computer respectively controls scanning operations at the first state of the angle of irradiation and at the second state of the angle of irradiation on a same line of scanning on the sample such that the first sample image and the second sample image are obtained and displayed on a real time basis, and
wherein the computer displays, on the display, a second button to select a stereoscopic observation using a stereoscopic liquid crystal display in which first image data obtained at the first state of the angle of irradiation and second image data obtained at the second state of the angle of irradiation are inputted in accordance with a pixel arrangement of the stereoscopic liquid crystal display, wherein the computer respectively controls scanning operations at the first state of the angle of irradiation and at the second state of the angle of irradiation on a same line of scanning on the sample such that the first sample image and the second sample image are obtained and displayed on a real time basis.

2. A charged particle beam device according to claim 1, wherein by using the first sample image obtained at the first state of the angle of irradiation and the second sample image obtained at the second state of the angle of irradiation, a stereoscopic image of said sample as viewed from obliquely above can be observed.

3. A charged particle beam device according to claim 1, wherein a table for prescribing current values passed to said deflector in accordance with tilting directions of said primary-electron beam is stored.

4. A charged particle beam device according to claim 1, wherein a stigmator adapted to correct the primary-charged particle beam for astigmatism, is disposed on the side of deflector opposing said charged particle source.

5. A charged particle beam device according to claim 1 further comprising:
a condenser lens on the side of the tilt deflector opposing said charged particle source, wherein an off-axis aberration generated in said objective lens is cancelled out by means of said condenser lens.

* * * * *